(12) United States Patent
Schon et al.

(10) Patent No.: US 6,572,620 B1
(45) Date of Patent: Jun. 3, 2003

(54) MODULAR, BLADE-ROD, INTRAMEDULLARY FIXATION DEVICE

(76) Inventors: Lew C. Schon, 2917 Old Court Rd., Baltimore, MD (US) 21208; Brent G. Parks, 2731 Wynfield Rd., West Friendship, MD (US) 21794; Christopher Chiodo, 261 Dean St., Apt. B, Norwood, MA (US) 02062

( * ) Notice: Subject to any disclaimer, the term of this patent is extended or adjusted under 35 U.S.C. 154(b) by 46 days.

(21) Appl. No.: 09/993,101

(22) Filed: Nov. 16, 2001

(51) Int. Cl.$^7$ .............................................. A61B 17/56
(52) U.S. Cl. .............................. 606/62; 606/64; 606/60
(58) Field of Search ........................... 606/60, 62, 63, 606/64, 65, 68, 67, 66

(56) References Cited

U.S. PATENT DOCUMENTS

| | | | | |
|---|---|---|---|---|
| 4,103,683 A | * | 8/1978 | Neufeld ........................ | 606/67 |
| 4,946,459 A | * | 8/1990 | Bradshaw et al. ............. | 606/62 |
| 4,978,349 A | * | 12/1990 | Frigg ............................ | 606/67 |
| 5,356,410 A | | 10/1994 | Pennig ......................... | 606/62 |
| 5,562,667 A | | 10/1996 | Shuler et al. ................. | 606/64 |
| 5,871,485 A | | 2/1999 | Rao et al. ..................... | 606/65 |
| 5,928,235 A | | 7/1999 | Friedl ........................... | 606/64 |
| 6,007,536 A | | 12/1999 | Yue ............................... | 606/60 |
| 6,077,264 A | | 6/2000 | Chemello ..................... | 606/67 |
| 6,139,552 A | | 10/2000 | Horiuchi ....................... | 606/88 |
| 6,224,606 B1 | | 5/2001 | Horiuchi ....................... | 606/88 |
| 6,231,576 B1 | | 5/2001 | Frigg et al. ................... | 606/62 |
| 6,235,031 B1 | | 5/2001 | Hodgeman et al. ........... | 606/64 |

* cited by examiner

Primary Examiner—Pedro Philogene
(74) Attorney, Agent, or Firm—Larry J. Guffey

(57) ABSTRACT

The intramedullary fixation device for use in fixing the relative position between a tubular bone and an adjoining bone has, according to the present invention, an intramedullary nail intramedullary nail that is inserted into the medullary canal of the tubular bone whose position is to be fixed, an elongated blade for insertion into the adjoining bone whose position is to be fixed relative to that of the tubular bone, a washer for use when the nail's design is such that its end section is not perpendicular to its longitudinal axis, and a screw that passes through openings in the blade and washer and into a threaded bore in the nail so as to, when tightened, lock the screw, washer, blade and nail together so as to prevent relative movement between these elements. The related method of the present invention comprises the steps of providing the listed elements for the fixation device and then seating the intramedullary nail and blade in the respective tubular and adjoining bones, and inserting the fixation means through a blade passageway and into a nail threaded bore so as to lock the elements together and to prevent relative movement between the treated bones.

28 Claims, 4 Drawing Sheets

MODULAR, BLADE-ROD, INTRAMEDULLARY FIXATION DEVICE

BACKGROUND OF THE INVENTION

1. Field of the Invention

This invention relates to improved internal fixation means used in surgical procedures to treat fractured bones, pending fractures of bones, non-unions, arthritis, as well as any other procedure in which an attempt is made to surgically fuse two or more bones. More particularly, this invention relates to an orthopedic surgical implant and its method of use for stabilizing the relative position between a bone having a medullary canal and an adjoining bone or bone section.

2. Description of the Related Art

In recent years, both solid and tubular, metal rods or intramedullary nails have gradually gained importance in orthopedic surgery. They have in many situations become the standard surgical implant for stabilizing fractures or pending fractures in large tubular bones, such as the femur (thigh bone), tibia (leg bone) or humerus (upper arm bone).

The shape and configuration of such intramedullary nails has been a topic of much inventive effort. From initially circular or almost circular cross-sections, these nails have, in order to minimize the damage done to the bone during their placement in the body, come to be designed such that their cross-sections correspond to the anatomy of the medullary canals in which they are to be used.

For example, for the humerus bone, in which the medullary canal is not round along its entire length but is in fact flat and thin in the distal part, a nail with a flattened cross-section for its distal end has been developed. See U.S. Pat. No. 6,231,576.

In order to avoid the rotation of bone fragments and their shortening in multifragmented fractures, these nails have come to be used with various accessories, such as anchoring screws and other elongated, blade-like elements, that pass through holes in such nails and attach to the various bone fragments. See U.S. Pat. Nos. 5,928,235, 6,077,264, 6,235,031 and 5,562,667 for examples of such elements and their methods of use for stabilizing fractures of the neck of the femur.

Despite the extensive development of such intramedullary nails and accessories, they continue to exhibit certain disadvantages. For example, their designs are such that: (1) they often offer only minimal flexibility in addressing situations in which the bones or bone fragments to be stabilized have unique geometries or orientations, (2) they often involve relatively complex designs which tend to increase their costs of manufacture, and (3) their uses have heretofore been confined primarily to the treatment of fractures and pending fractures in individual large, tubular bones and for limited fusions of the ankle and knee - they have also been used in situations to stabilize one or several bones, but (4) they do not provide stability in all three, orthogonal planes of motion. Thus, there exists a continuing need for the development of new and improved intramedullary fixation devices.

SUMMARY OF THE INVENTION

Recognizing the need for the development of improved intramedullary fixation means, the present invention is generally directed to satisfying the needs set forth above and overcoming the disadvantages identified with prior art devices.

In accordance with one preferred embodiment of the present invention, the foregoing need can be satisfied by providing an intramedullary fixation device for use in fixing the relative position between a bone having a medullary canal and an adjoining bone or section of bone. Such a device comprises: (1) an intramedullary nail that is to be inserted into the medullary canal of the tubular bone whose position is to be fixed, with this nail having distal and proximate ends, a longitudinal axis extending between the ends, the proximate end terminating in a proximate end cross section that intersects the longitudinal axis of the nail, a threaded bore that extends from the proximate end cross section and along a specified portion of the longitudinal axis of the nail, and an opening situated along the length of the nail and extending through the nail and thorough which additional support screws or other attachment means can pass for further fixing the position of the nail, (2) an elongated blade for insertion into the adjoining bone whose position is to be fixed relative to that of the tubular bone, with this blade having distal and proximate ends, a longitudinal axis extending between these ends, top and bottom surfaces that extend between the ends, a passageway adjacent the proximate end that extends between the top and bottom surfaces, with the blade proximate end being configured so as to aid the passage of this end through the bone, and with the angle of intersection of the nail proximate end cross section with the nail's longitudinal axis being chosen so as to set the desired angle of intersection between the longitudinal axes of the nail and blade, (3) a washer for use when the nail's design is such that its proximate end section is not perpendicular to its longitudinal axis, with this washer having a top and a bottom surface, a longitudinal axis extending between these washer surfaces and an aperture extending between these surfaces, with the washer top surface being oriented so that it intersects the washer's longitudinal axis at an angle which is complementary to the angle of intersection of the nail proximate end section with the nail's longitudinal axis so as to allow the longitudinal axes of the washer and nail to coincide when the washer top surface fully contacts the nail's proximate end section, and (4) a screw having a threaded section and a screw head, the threaded section configured so as to allow the screw to extend through the washer and blade passageway and into the nail's threaded bore, with the screw head configured so that when the threaded section is fully screwed into the nail's threaded bore the screw head presses against the washer's bottom surface so as to lock the screw, washer, blade and nail together so as to prevent relative movement between these elements.

According to a second embodiment of the present invention, the intramedullary fixation device further comprises the blade distal end terminating in a distal end cross section that intersects the longitudinal axis of the blade. An orifice extends from this distal end cross section, between the blade's top and bottom surfaces, and parallel to a specified portion of the longitudinal axis of the blade. This orifice is provided in order to allow for the initial insertion of a guide pin that is used to guide the precise placement of the blade in the adjoining bone.

According to a third embodiment of the present invention, a method is provided for stabilizing a specified, relative position between a tubular bone having a medullary canal and an adjoining bone or section of bone. This method comprises the steps of providing the listed elements for the fixation device and then seating the intramedullary nail and blade in the respective tubular and adjoining bones, and inserting the fixation means through a blade passageway and into a nail threaded bore so as to lock the elements together and prevent relative movement between the treated bones.

There has been summarized above, rather broadly, the more important features of the present invention in order that the detailed description that follows may be better understood and appreciated. In this regard, it is instructive to also consider the objectives of the present invention.

Thus, it is an object of the present invention to provide an intramedullary fixation device and method that offers maximum flexibility in addressing situations in which the bones or bone fragments to be stabilized have unique geometries or orientations.

It is another object of the present invention to provide an intramedullary fixation device that is simple to construct and use and whose manufacturing costs may be kept to a minimum.

It is yet another object of the present invention to provide an intramedullary fixation device and method that can be used for treating situations other than just the treatment of fractures and pending fractures in individual large, tubular bones. For example, to treat the situation in which the position of two or more adjoining bones are stabilized in order to allow and promote surgical fusion, or arthrodesis, of these bones. Some examples of such non-fracture, clinical applications include arthritis, infection, neuropathy and deformity.

It is a further object of the present invention to provide a method and device for providing stabilization of the relative position between two or more bones that may or may not share adjacent surfaces (e.g., the tibia, talus and calcaneus).

It is a still further object of the present invention to provide a device and method that will advance the utility of intramedullary nails in orthopedic medicine.

These and other objects and advantages of the present invention will become readily apparent as the invention is better understood by reference to the accompanying drawings and the detailed description that follows.

Thus, there has been summarized above, rather broadly, the more important features and objectives of the present invention in order that the detailed description that follows may be better understood and appreciated. There are, of course, additional features of the invention that will be described hereinafter and which will form the subject matter of any eventual claims to this invention.

DESCRIPTION OF THE PREFERRED EMBODIMENT

Figure 1:
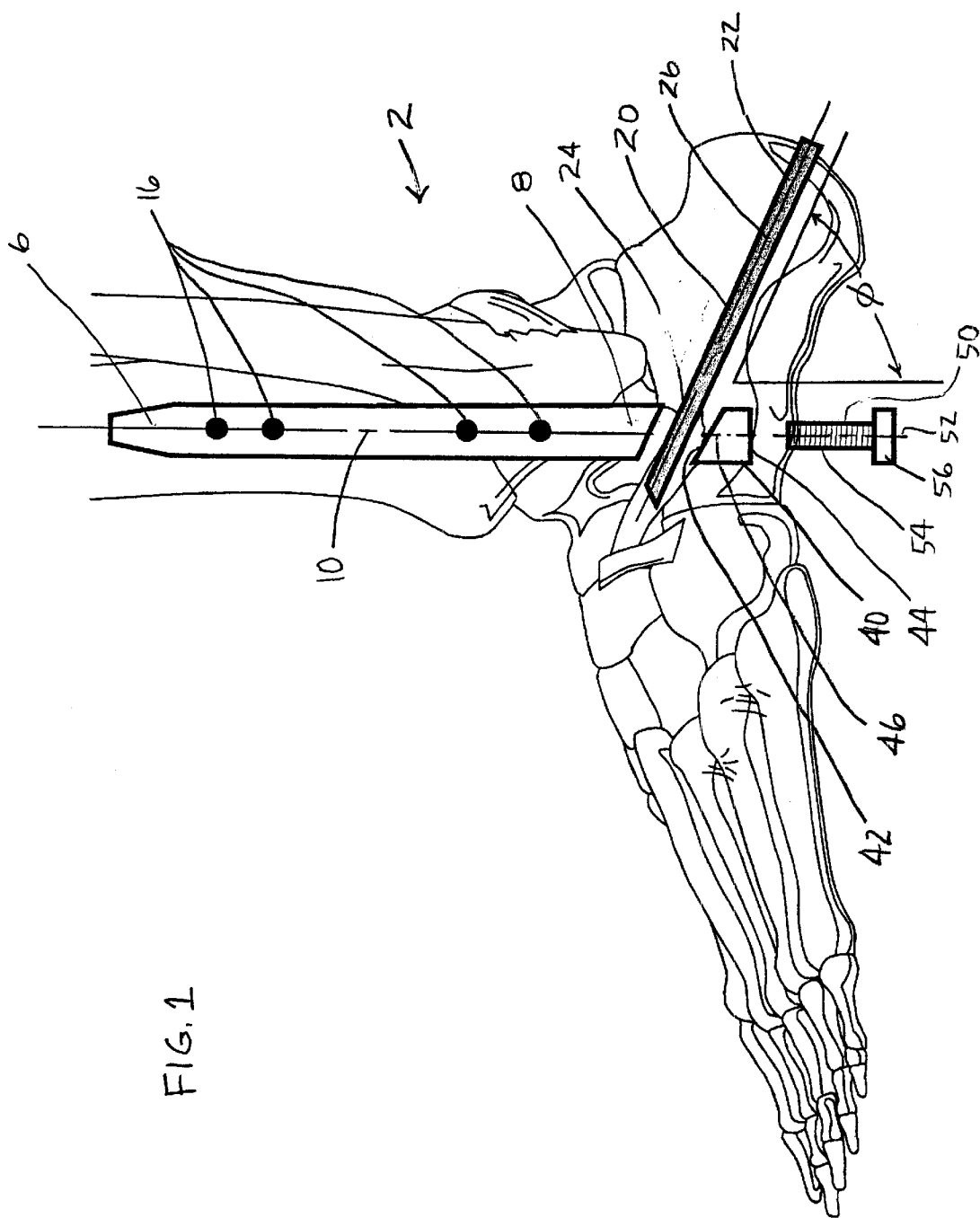
FIG. 1 is a plan view of a preferred embodiment of the present invention when it is being used to stabilize the position of the shin bone (tibia) relative to the adjoining ankle bone (talus).

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

Referring now to the drawings wherein are shown preferred embodiments and wherein like reference numerals designate like elements throughout, there is shown in FIG. 1 an illustration which depicts the situation in which an embodiment of the intramedullary fixation device 2 of the present invention is being used to stabilize the position of the shin bone (tibia) relative to the adjoining ankle (talus) and heel (calcaneus) bones. This embodiment is seen to consist of an intramedullary nail 4 that has been inserted through the bottom of the foot and into the medullary canal of the tibia. This nail 4 has distal 6 and proximate 8 ends, with a longitudinal axis 10 extending between these ends. The proximate end terminates in a proximate end cross section 12 that intersects the longitudinal axis 10 of the nail 4.

A threaded bore 14 extends from the proximate end cross section 12 and along a specified portion of the longitudinal axis 10 of the nail. The nail 4 further includes one or more openings 16 that are situated along the length of the nail 4 and extend through the nail 4. These openings are used to help fasten additional support screws or other attachment means that can pass through the openings for providing further stabilization means for the nail 4.

The precise shape and configuration of this intramedullary nail 4 is set, in order to minimize the damage done to the bone during its placement in the body, so that its cross sectional shape corresponds to the anatomy of the medullary canal in which it is to be used. For the present application involving stabilization of the talus and tibia, the nail's cross sectional shape is circular or almost circular. Other applications might call for the use of nails having a wide variety of shapes (e.g., polygonal cross sections with assorted curvature in their longitudinal direction).

Figure 2:
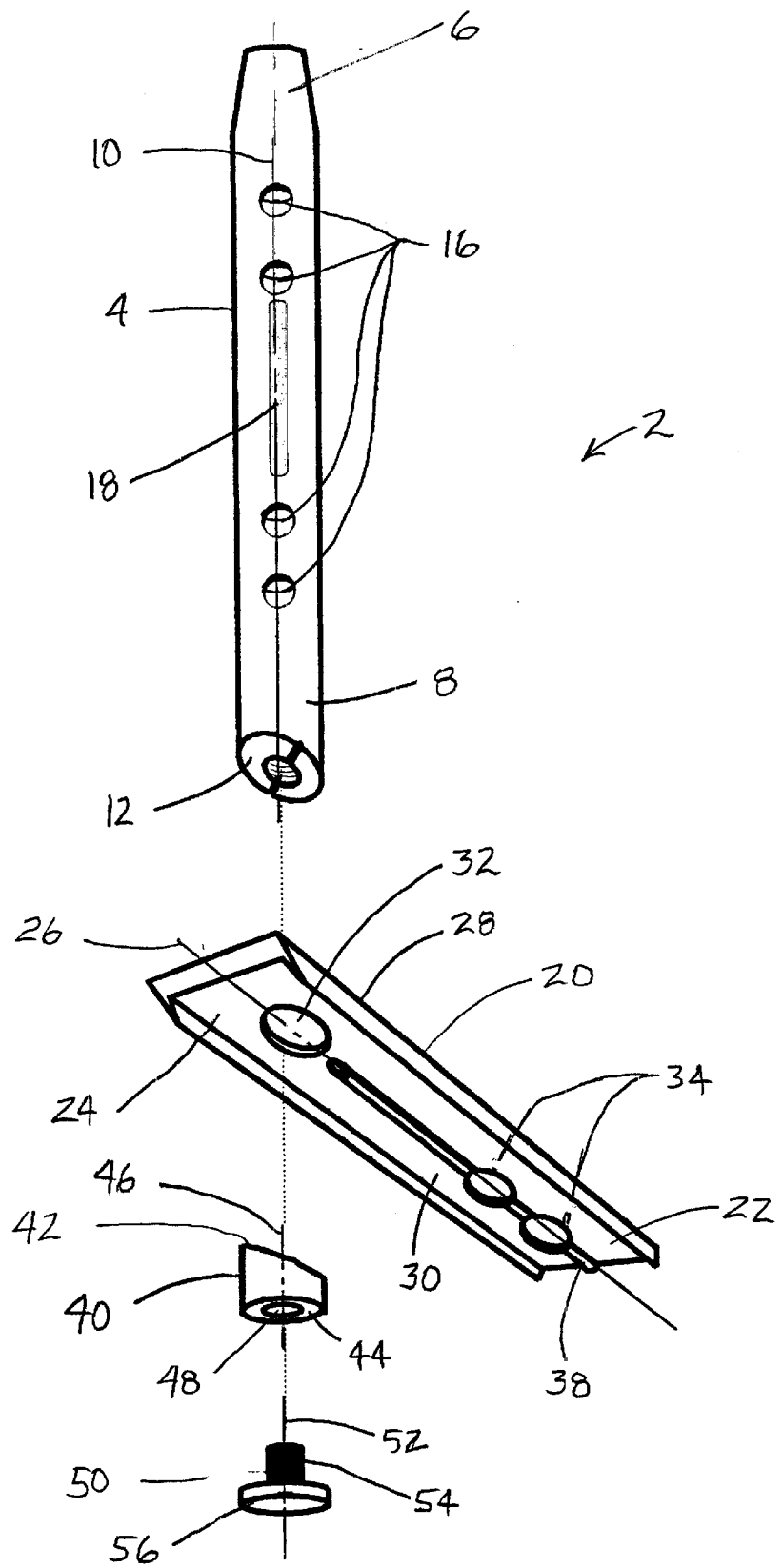
FIG. 2 is an exploded perspective view of the elements that comprise the preferred embodiment shown in FIG. 1.

To provide such nails with the flexibility to be used in a wider range of fracture treatment situations, the nail's length can be made expandable by the inclusion at a point along the length of the nail 4 of a known-in-the-art, internal turnbuckle mechanism 18. See FIG. 2.

An elongated blade 20 is seen to have been driven through the adjoining ankle bone whose position is to be fixed relative to that of the tibia. This blade 20 has a distal 22 end and a sharpened proximate 24 end, with a longitudinal axis 26 and top 28 and bottom 30 surfaces that extends between these ends. A passageway 32 adjacent the proximate end extends between the blade's top 28 and bottom 30 surfaces, and thereby provides a passage through which a screw 50 may be passed in order to lock the blade 20 and nail 4 together. The angle of intersection of the nail's proximate end cross section 12 with the nail's longitudinal axis 10 is fixed so as to set the desired angle of intersection, $\phi$, between the longitudinal axes of the nail and blade 10, 26. The blade 20 further includes one or more openings 34 that are situated along the length of the blade 20 and extend through the blade 20. These openings 34 are used to help fasten additional support screws or other attachment means that can pass through the openings 34 for providing further stabilization means for the blade 20.

The blade distal end 22 terminates in a distal end cross section 36 that intersects the longitudinal axis 26 of the blade. An orifice 38 extends from this distal end cross section 36 and along a specified portion of the longitudinal axis 26 of the blade. This orifice 38 is provided in order to allow for the initial insertion of a guide pin 80 that is used to guide the precise placement of the blade 20 in the bone, and for the later extraction of the blade 30 from the bone.

Figure 3A:
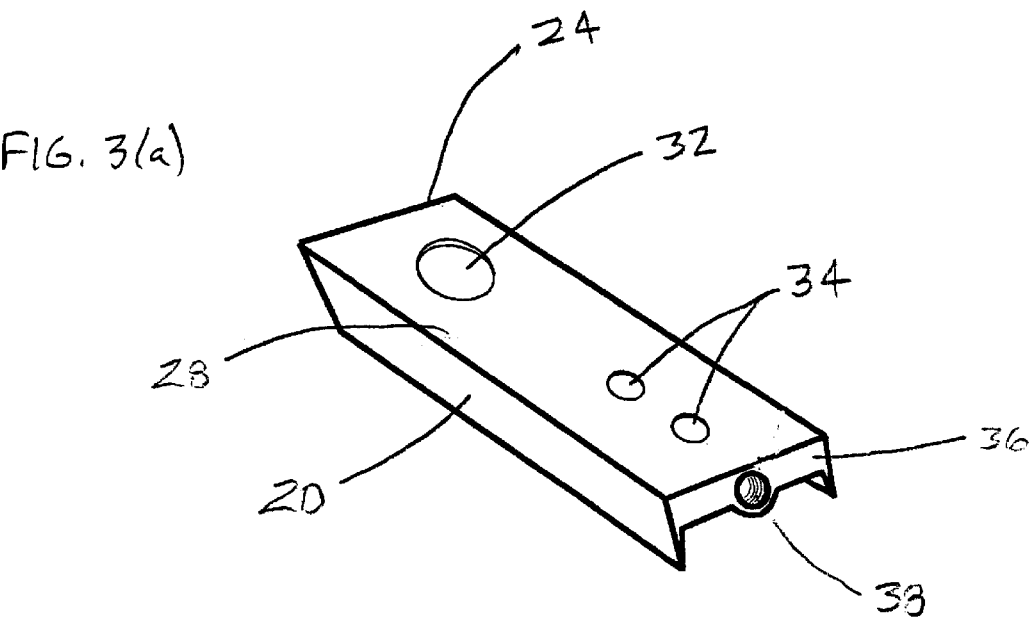
FIG. 3(a) is a perspective, end view of a preferred embodiment of the present invention's elongated blade.
Figure 3B:
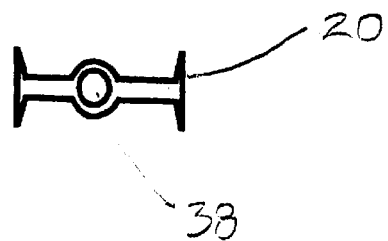
FIG. 3(b) is a second preferred embodiment for the shape of the cross sectional section of the present invention's elongated blade.

The shape and configuration of this blade's cross section will vary depending upon the geometry and nature of the bones to be treated. FIGS. 3(*a*)–3(*b*) display alternative blade geometries that have been found to be useful in treating the situation depicted in FIG. 1.

When the nail's design is such that its proximate end section 12 is not perpendicular to its longitudinal axis 10, a washer 40 is used to align the longitudinal axes of the nail 10 and the screw 52 when the washer's top surface 42 is in contact with the nail's proximate end section 12. This washer 40 also has a bottom surface 44 and a longitudinal axis 46 and an aperture 48 extending between the washer's surfaces.

The screw 50 for locking these elements together has a threaded section 54 and a screw head 56. This threaded section 54 is configured so as to allow the screw 50 to extend through the washer aperture 48 and blade passageway 32 and into the nail's threaded bore 14, with the screw head 56 configured so that, when the threaded section 54 is fully screwed into the nail's threaded bore 14, the screw head 56 presses against the washer's bottom surface 44 so as to lock the screw 50, washer 40, blade 20 and nail 4 together so as to prevent relative movement between these elements. In some applications, it may prove useful to provide the interfacing surfaces of these elements with surface contours or protrusions and corresponding indentations as to allow interdigation between the elements so as to enhance the degree of locking achieved between the elements.

Although the above-discussed, preferred embodiment uses a threaded bore 14 and screw 50 to lock the nail 4 and blade 20 together, it should be recognized that there many alternative coupling elements that can be used to perform this same function. Thus, these alternative, coupling elements should be considered to be within the scope of the present invention.

Figure 4:
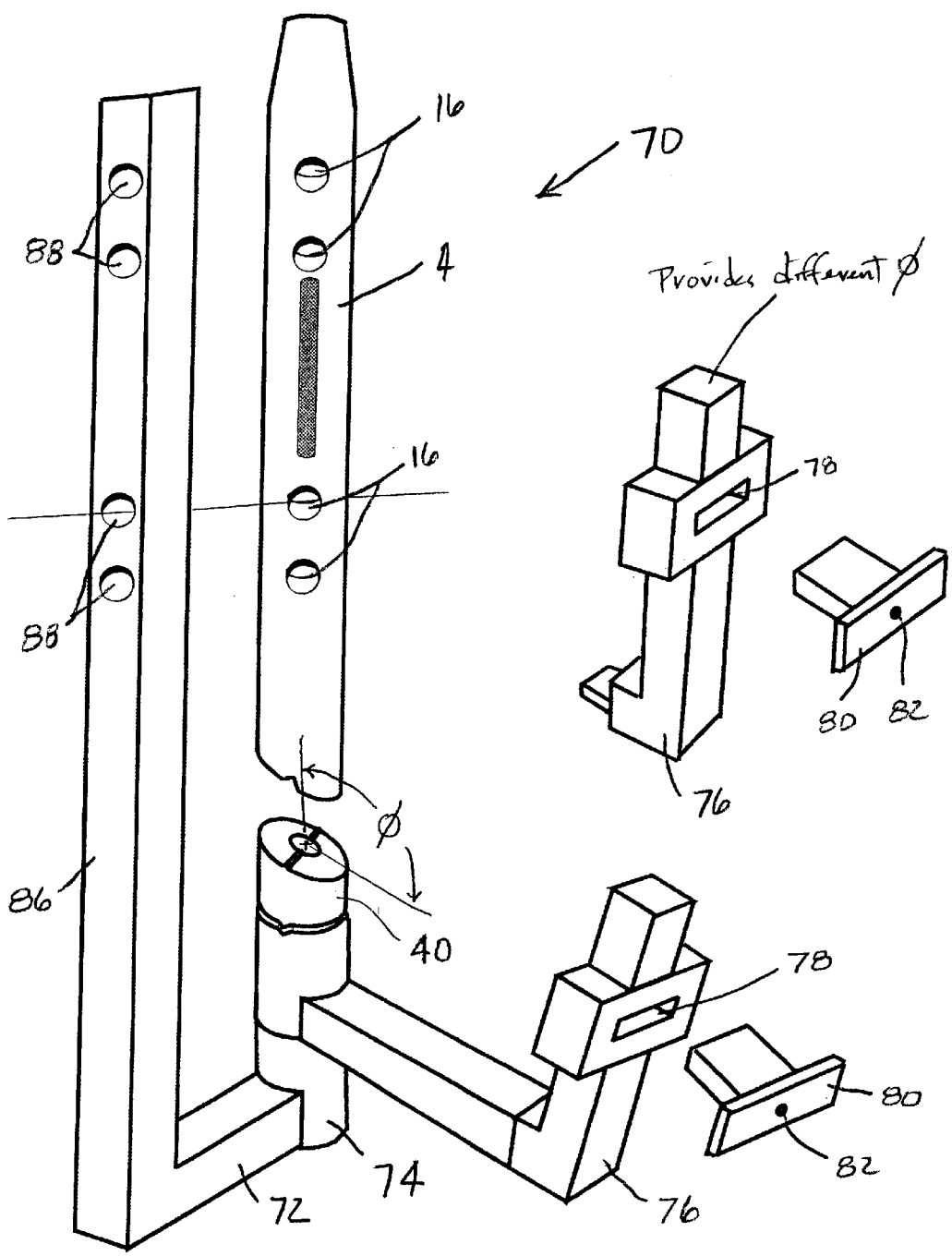
FIG. 4 is a perspective view of an alignment apparatus which is used to locate and precisely position within the bones to-be-treated the nail and blade of the present invention.

FIG. 4 provides a perspective view of an alignment apparatus 70 that is used to locate and precisely position within the bones to-be-treated the nail 4 and blade 20 of the present invention. It consists of a base portion 72 having a seat portion 74 upon which the to-be-inserted nail 4 and washer 40 may be aligned and positioned prior to insertion. It also includes a detachable, blade alignment section 76 that has an orifice 78 through which the blade is passed for insertion into the targeted bone. Into this orifice 78 can also be inserted a guidewire adapter 80 which contains an orifice 82 in which a guide pin 84 can be placed and then fed into the precise position where the blade is to-be-inserted into the bone.

This blade alignment section 76 is detachable so that any one of a group of such especially designed sections can be used with the alignment apparatus 70. These sections 76 differ in their configurations, with these being chosen so as to provide for the desired angular orientation between the implanted nail and blade.

The alignment apparatus 70 further has a tower section 86 in which are located additional holes 88 which serve to locate and align with the openings 16 that are situated along the length of the nail 4. These holes 88 are used to help fasten additional support screws or other attachment means for providing further stabilization means for the nail 4.

Although the foregoing disclosure relates to preferred embodiments of the invention, it is understood that these details have been given for the purposes of clarification only. Various changes and modifications of the invention will be apparent, to one having ordinary skill in the art, without departing from the spirit and scope of the invention as hereinafter set forth in the claims.

We claim:

1. An intramedullary fixation device comprising:

an intramedullary nail having distal and proximate ends, a longitudinal axis extending between said ends, said proximate end terminating in an end cross section that intersects the longitudinal axis of said nail, a blade having distal and proximate ends, a longitudinal axis extending between said ends, top and bottom surfaces that extend between said ends, and a passageway adjacent said proximate end that extends between said top and bottom surfaces, a first coupling element fixed on said nail end cross section, and a second coupling element configured so as to allow a portion of said second coupling element to extend through said blade passageway and interact with said first coupling element so as to lock said coupling elements together and prevent relative movement between said nail and blade.

2. An intramedullary fixation device as recited in claim 1, wherein:

the angle of intersection of said nail proximate end cross section with said nail's longitudinal axis is chosen so as to set the desired angle of intersection between the longitudinal axes of said nail and blade, and said fixation device further comprising a washer having a top and a bottom surface, a longitudinal axis extending between said washer surfaces and an aperture extending between said surfaces and configured to allow the passage of said portion of said second coupling element through said aperture, said washer top surface being oriented so that it intersects said washer longitudinal axis at an angle which is complementary to the angle of intersection of said nail proximate end cross section with said nail's longitudinal axis so as to allow the longitudinal axes of said washer and nail to coincide when said washer top surface fully contacts said nail proximate end section.

3. An intramedullary fixation device as recited in claim 1, wherein:

said blade distal end terminating in an end cross section that intersects the longitudinal axis of said blade, an orifice that extends from said blade end cross section, between said top and bottom surfaces, and parallel to a specified portion of the longitudinal axis of said blade.

4. An intramedullary fixation device as recited in claim 2, wherein:

said blade distal end terminating in an end cross section that intersects the longitudinal axis of said blade, an orifice that extends from said blade end cross section, between said top and bottom surfaces, and parallel to a specified portion of the longitudinal axis of said blade.

5. An intramedullary fixation device as recited in claim 1, wherein:

said blade proximate end being configured so as to aid the passage of said end through a bony material.

6. An intramedullary fixation device as recited in claim 2, wherein:

said blade proximate end being configured so as to aid the passage of said end through a bony material.

7. An intramedullary fixation device as recited in claim 3, wherein:

said blade proximate end being configured so as to aid the passage of said end through a bony material.

8. An intramedullary fixation device as recited in claim 4, wherein:

said blade proximate end being configured so as to aid the passage of said end through a bony material.

9. An intramedullary fixation device as recited in claim 5, wherein:

said nail having an opening situated along the length of said nail and extending through said nail and intersecting the longitudinal axis of said nail.

10. An intramedullary fixation device as recited in claim 6, wherein:

said nail having an opening situated along the length of said nail and extending through said nail and intersecting the longitudinal axis of said nail.

11. An intramedullary fixation device as recited in claim 7, wherein:

said nail having an opening situated along the length of said nail and extending through said nail and intersecting the longitudinal axis of said nail.

12. An intramedullary fixation device as recited in claim 8, wherein:

said nail having an opening situated along the length of said nail and extending through said nail and intersecting the longitudinal axis of said nail.

13. An intramedullary fixation device as recited in claim 9, wherein:

said first coupling element comprising a threaded bore that extends from said end cross section and along a specified portion of the longitudinal axis of said nail, and said second coupling element having a threaded section and a head, said head configured so as to not allow said head to pass through said blade passageway so that when said threaded section is fully screwed into said nail threaded bore the head presses against said blade bottom surface so as to lock said second coupling element, blade and nail together so as to prevent relative movement between said elements.

14. An intramedullary fixation device as recited in claim 10, wherein:

said first coupling element comprising a threaded bore that extends from said end cross section and along a specified portion of the longitudinal axis of said nail, and said second coupling element having a threaded section and a head, said head configured so as to not allow said head to pass through said blade passageway so that when said threaded section is fully screwed into said nail threaded bore the head presses against said blade bottom surface so as to lock said second coupling element, blade and nail together so as to prevent relative movement between said elements.

15. An intramedullary fixation device as recited in claim 11, wherein:

said first coupling element comprising a threaded bore that extends from said end cross section and along a specified portion of the longitudinal axis of said nail, and said second coupling element having a threaded section and a head, said head configured so as to not allow said head to pass through said blade passageway so that when said threaded section is fully screwed into said nail threaded bore the head presses against said blade bottom surface so as to lock said second coupling element, blade and nail together so as to prevent relative movement between said elements.

16. An intramedullary fixation device as recited in claim 12, wherein:

said first coupling element comprising a threaded bore that extends from said end cross section and along a specified portion of the longitudinal axis of said nail, and said second coupling element having a threaded section and a head, said head configured so as to not allow said head to pass through said blade passageway so that when said threaded section is fully screwed into said nail threaded bore the head presses against said blade bottom surface so as to lock said second coupling element; blade and nail together so as to prevent relative movement between said elements.

17. An intramedullary fixation device as recited in claim 13, further comprising:

a means for locating and positioning within the bones to-be-treated said nail and said blade.

18. An intramedullary fixation device as recited in claim 14, further comprising:

a means for locating and positioning within the bones to-be-treated said nail and said blade.

19. An intramedullary fixation device as recited in claim 15, further comprising:

a means for locating and positioning within the bones to-be-treated said nail and said blade.

20. An intramedullary fixation device as recited in claim 16, further comprising:

a means for locating and positioning within the bones to-be-treated said nail and said blade.

21. A method for providing stabilization means for use in fixing the specified, relative position between a tubular bone having a medullary canal and an adjoining bone or section of bone, said method comprising the steps of:

providing an intramedullary nail having distal and proximate ends, a longitudinal axis extending between said ends, said proximate end terminating in an end cross section that intersects the longitudinal axis of said nail, and a threaded bore that extends from said end cross section and along a specified portion of the longitudinal axis of said nail, providing a blade having distal and proximate ends, a longitudinal axis extending between said ends, top and bottom surfaces that extend between said ends, and a passageway adjacent said proximate end that extends between said top and bottom surfaces, providing a fixation means configured so as to allow said means to extend through said blade passageway and into said nail threaded bore, seating said intramedullary nail in said tubular bone, seating said blade in said adjoining bone such that its longitudinal axis intersects the longitudinal axis of said nail so as to provide said specified, relative position between said tubular bone and said adjoining bone, inserting said fixation means through said blade passageway and into said nail threaded bore so as to lock said fixation means, blade and nail together so as to prevent relative movement between said elements.

22. The treatment method as recited in claim 21, further comprising the step of:

providing a washer having a top and a bottom surface, a longitudinal axis extending between said washer surfaces and an aperture extending between said surfaces and configured to allow the passage of said fixation means through said aperture, said washer top surface being oriented so that it intersects said washer longitudinal axis at an angle which is complementary to the angle of intersection of said nail proximate end cross section with said nail's longitudinal axis so as to allow the longitudinal axes of said washer and nail to coincide when said washer top surface fully contacts said nail proximate end section, wherein the angle of intersection of said nail proximate end cross section with said nail's longitudinal axis is chosen so as to set the necessary angle of intersection between the longitudinal axes of said nail and blade so as to yield said specified, relative position between said tubular bone and adjoining bone.

23. The treatment method as recited in claim 21, further comprising the steps of:

providing a means for locating and positioning within said tubular and adjoining bone said nail and blade, and utilizing said locating and positioning means to seat said nail in said tubular bone and to sear said blade in said adjoining bone.

24. The treatment method as recited in claim 22, further comprising the steps of:

providing a means for locating and positioning within said tubular and adjoining bone said nail and blade, and utilizing said locating and positioning means to seat said nail in said tubular bone and to sear said blade in said adjoining bone.

25. The treatment method as recited in claim 21 wherein the tubular bone is the tibia and the adjoining bone is the talus.

26. The treatment method as recited in claim 22 wherein the tubular bone is the tibia and the adjoining bone is the talus.

27. The treatment method as recited in claim 23 wherein the tubular bone is the tibia and the adjoining bone is the talus.

28. The treatment method as recited in claim 24 wherein the tubular bone is the tibia and the adjoining bone is the talus.

* * * * *